US010415073B2

(12) United States Patent
Driscoll

(10) Patent No.: US 10,415,073 B2
(45) Date of Patent: Sep. 17, 2019

(54) KIT COMPRISING ATP-DIPHOSPHOHYDROLASE FOR DETECTING BACTERIAL ATP IN A SAMPLE

(71) Applicant: 3M INNOVATIVE PROPERTIES COMPANY, Saint Paul, MN (US)

(72) Inventor: Mark B. Driscoll, Pontypridd (GB)

(73) Assignee: 3M Innovative Properties Company, St. Paul, MN (US)

( * ) Notice: Subject to any disclaimer, the term of this patent is extended or adjusted under 35 U.S.C. 154(b) by 109 days.

(21) Appl. No.: 15/526,087

(22) PCT Filed: Nov. 9, 2015

(86) PCT No.: PCT/US2015/059654
§ 371 (c)(1),
(2) Date: May 11, 2017

(87) PCT Pub. No.: WO2016/077185
PCT Pub. Date: May 19, 2016

(65) Prior Publication Data
US 2017/0306384 A1    Oct. 26, 2017

Related U.S. Application Data

(60) Provisional application No. 62/079,156, filed on Nov. 13, 2014.

(51) Int. Cl.
*C12Q 1/42* (2006.01)
*C12Q 1/00* (2006.01)
*C12Q 1/34* (2006.01)
*C12Q 1/66* (2006.01)

(52) U.S. Cl.
CPC .............. *C12Q 1/008* (2013.01); *C12Q 1/34* (2013.01); *C12Q 1/42* (2013.01); *C12Q 1/66* (2013.01); *C12Y 306/01005* (2013.01); *G01N 2333/914* (2013.01)

(58) Field of Classification Search
None
See application file for complete search history.

(56) References Cited

U.S. PATENT DOCUMENTS

| 6,730,685 B1 | 5/2004 | Brülls |
| 7,888,059 B2 | 2/2011 | Karlish |
| 2003/0157590 A1 | 8/2003 | Foote |

FOREIGN PATENT DOCUMENTS

| JP | 10-191972 | * 7/1998 |
| WO | WO 2004-035818 | 4/2004 |
| WO | WO 2014-052848 | 4/2014 |

OTHER PUBLICATIONS

Barr, "The Preservation of Aqueous Sorbitol Solutions"; Journal of the American Pharmaceutical Association; 1957, vol. 46; No. 4; pp. 221-223 (XP55240383).
Davenport, "Rapid Testing of Non-Dairy and Mixed Dairy Beverages Using the 3M™ Microbial Luminescence System (MLS, formerly Cogent)"; 3M 2009; 1 pg.
Griffiths, "Applications of Bioluminescence in the Dairy Industry"; Journal of Dairy Science; 1993, vol. 76, No. 10; pp. 3118-3125.
Karamohamed, "Research Report—Bioluminometric Method for Real-Time Detection of ATPase Activity"; BioTechniques; 2001, vol. 31, No. 2; pp. 420-425.
Matouschek, "Cyclophilin catalyzes protein folding in yeast mitochondria"; Proceedings of the National Academy of Sciences; 1995, vol. 92; pp. 6319-6323 (XP55240391).
Sanyal, "Import of Transcription Factor MTF1 into the Yeast Mitochondria Takes Place through an Unusual Pathway"; The Journal of Biological Chemistry; 1995, vol. 270, No. 20, pp. 11970-11976 (XP55240388).
Yoo, "Thermoprotective Effect of Sorbitol on Proteins during Dehydration"; J. Agric. Food Chem.; 1993, vol. 41, No. 2; pp. 190-192.
Product Information on Apyrase from NEB retrieved on Aug. 24, 2014 from https://www.neb.com/products/M0393-apyrase; 3 pgs.
Product Information on Apyrase from Sigma-Aldrich, Inc.; retrieved on Aug. 28, 2014; 1 pg.
Product Specification on Apyrase from Sigma-Aldrich; retrieved on Aug. 28, 2014; 1 pg.
International Search report for PCT International Application No. PCT/US2015/059654 dated Jan. 22, 2016, 5 pages.

* cited by examiner

*Primary Examiner* — Jennifer E Graser
(74) *Attorney, Agent, or Firm* — Eric E. Silverman

(57) ABSTRACT

A kit for detecting bacterial ATP in a sample is provided. The kit comprises an aqueous composition having a pH of about 6.0 to 7.2. The aqueous composition comprises effective amounts of a polyol, a buffer reagent, a protein, and ATP-diphosphohydrolase. A method of using the kit to detect bacterial ATP is also provided.

19 Claims, No Drawings

KIT COMPRISING ATP-DIPHOSPHOHYDROLASE FOR DETECTING BACTERIAL ATP IN A SAMPLE

CROSS REFERENCE TO RELATED APPLICATIONS

This application is a national stage filing under 35 U.S.C. 371 of PCT/US2015/059654, filed Nov. 9, 2015, which claims the benefit of U.S. Provisional Application No. 62/079,156, filed Nov. 13, 2014, the disclosures of which are incorporated by reference in their entirety herein.

BACKGROUND

A wide variety of industrial products and other samples involved in industrial processes (raw materials, in-process samples, environmental samples etc.) need to be tested for microbial contamination. In some cases the final product must be sterile; in other cases a limit is set on the total number of micro-organisms allowed. Often tests are performed for the presence of certain specific organisms, and again the requirement may be absence in a particular amount of sample or there may be a limit on the number allowed.

Traditionally these tests involve use of culture techniques. However, these traditional testing methods are slow. Typically, it usually takes at least 24 hours before healthy, fast-growing bacteria or yeasts form colonies large enough to comfortably count on an agar plate. However, many samples contain stressed micro-organisms that need a recovery period before they begin to multiply, or organisms (including molds) which grow slowly on common types of culture media. Therefore many validated culture methods require an incubation period of 24-48 hours and, in some cases, 5 days or more.

Many microbiological tests are now performed much more rapidly using an ATP bioluminescence reaction to detect ATP released from a cell (e.g., a microorganism cell). ATP is an essential part of energy metabolism and therefore an indicator of the presence of living organisms or other organic matter.

These tests make use of the luciferase enzyme. A bioluminescence reagent contains luciferase with; inter alia, its substrate luciferin, magnesium ions and a suitable buffer. When adenosine-5'-triphosphate (ATP) is added to this reagent, luciferase catalyzes the emission of light. The result of the test is recorded as an RLU (relative light unit) value. The RLU value generally is proportional to the quantity of microorganisms present in a test sample.

Certain samples (e.g., milk) may contain relatively high levels of free ATP associated with casein micelles and ATP present in somatic cells. In these situations, chelating agents can be used to disrupt the micelles, mild detergents can be used to lyse the somatic cells, and the "nonmicrobial" ATP can be hydrolyzed using apyrase (an ATP-hydrolyzing enzyme); thereby enabling the detection of microbial ATP. There remains a need for simple, convenient tests to detect microbial ATP.

SUMMARY

The present disclosure relates to kits that comprise aqueous compositions of ATP-diphosphohydrolase that are exceptionally stable at ambient temperatures (e.g., about 25° C.) and a method of making said compositions. It is known that substantially dry compositions comprising ATP-diphosphohydrolase are stable at 0° C. It is known further that >1 mg/mL ATP-diphosphohydrolase can be stable in aqueous compositions (pH 5-7) when stored frozen. It is known even further that <1 mg/mL ATP-diphosphohydrolase can be stored in aqueous compositions (pH 7.5) comprising 1 mM $MgCl_2$, 1 mm DTT, 1 mM EDTA, and 1 mg/mL bovine albumin. However, it is also known that repeated freeze-thaw cycles and room temperature exposure for several hours leads to the loss of ATP-diphosphohydrolase activity in aqueous solutions. The composition can be used in kits for detecting bacterial ATP in a sample.

The inventive aqueous composition of the present disclosure surprisingly retains greater than or equal to about 90% of an initial ATP-diphosphohydrolase enzyme activity after at least 28 days of storage at room temperature (e.g., about 21-25° C.). Advantageously, this stabilization of ATP-diphosphohydrolase in an aqueous solution at ambient temperature permits the use of the aqueous composition in a kit for detecting ATP bioluminescence.

In one aspect, the present disclosure provides a kit comprising an aqueous composition having a pH of about 6.0 to 7.2. The aqueous composition can comprise effective amounts of a polyol, a buffer reagent, a protein, and ATP-diphosphohydrolase. In any embodiment, the polyol can comprise sorbitol, the buffer reagent can comprise a mixture of HEPES, Tris, and succinate, and the protein can comprise bovine serum albumin.

In another aspect, the present disclosure provides a method of retaining greater than or equal to 90% of an initial ATP-diphosphohydrolase enzyme activity in an aqueous composition stored above 0° C. for at least 7 days. The method can comprise forming an aqueous composition having a pH of about 6.0 to 7.2, the composition comprising effective amounts of a polyol, a buffer reagent, a protein, and ATP-diphosphohydrolase; and storing the aqueous composition at a temperature between 1-25° C., inclusive, for a period of at least 7 days. The aqueous composition has an initial concentration of ATP-diphosphohydrolase activity at a first time point. The combination of the effective amounts of the polyol, the buffer reagent, the protein, and the ATP-diphosphohydrolase enable retention of greater than or equal to 90% of the initial ATP-diphosphohydrolase activity after the composition is held at 25° C. from the first time point until a second time point that is 7 days after the first time point. The ATP-diphosphohydrolase activity is measured in a bioluminescent coupled assay at pH 7.75 with non-rate-limiting concentrations of ATP, luciferin, and luciferase. In any embodiment of the above method, the combination of the effective amounts of the polyol, the buffer reagent, the protein, and the ATP-diphosphohydrolase can enable retention of greater than or equal to 90% of the initial ATP-diphosphohydrolase activity after the composition is held at 25° C. from the first time point until a second time point that is 28 days after the first time point. In any of the above-embodiments of the method, the combination of the effective amounts of the polyol, the buffer reagent, the protein, and the ATP-diphosphohydrolase can enable retention of greater than or equal to 95% of the initial ATP-diphosphohydrolase activity after the composition is held at 25° C. from the first time point until the second time point.

The terms "comprises" and variations thereof do not have a limiting meaning where these terms appear in the description and claims.

As used herein, "a," "an," "the," "at least one," and "one or more" are used interchangeably. Thus, for example, a buffer reagent can be interpreted to mean "one or more" buffer reagents.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and from the claims.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is now known the aqueous composition of the present disclosure can be combined with luciferase, luciferin, and a source of ATP to detect live microorganisms in a sample. The aqueous composition can be used to remove "free" ATP from a sample before the microorganism cells, if present in the sample, are disrupted and ATP associated with the disrupted cells is detected in a bioluminescent enzymatic reaction. Surprisingly, the composition can retain at least 90% of initial apyrase activity after storage for a period of at least four weeks at or below ambient temperature.

The present disclosure provides a kit. In any embodiment, the kit can be used for detecting ATP associated with viable microorganisms. The kit comprises the components disclosed herein and, optionally, instructions for using the components. The kit comprises an aqueous composition having a pH of about 6.0 to about 7.2, the composition comprising effective amounts of a polyol, a buffer reagent, a protein, and ATP-diphosphohydrolase.

The aqueous composition of the present disclosure can be used in a method of detecting microbial ATP in a sample (e.g., milk). The aqueous composition is mixed (e.g., diluted) with a sample that may comprise non-microbial ATP. Thus, acellular (non-microbial) ATP is eliminated from the sample via the action of the ATP-diphosphohydrolase. Subsequently, the microorganisms, if present in the sample, are lysed and the microbial ATP can be detected using detection methods (e.g., ATP-dependent bioluminescence) that are known in the art.

Accordingly, the aqueous composition of the present disclosure comprises an amount (e.g., concentration) of ATP diphosphohydrolase such that, when mixed with the sample, is effective to hydrolyze ATP in the sample within a relatively short period of time (e.g., less than several hours, less than one hour, less than or equal to 30 minutes, less than or equal to 20 minutes, less than or equal to 15 minutes, less than or equal to 10 minutes, less than or equal to 5 minutes, less than or equal to 2 minutes, less than or equal to 1 minute, less than 1 minute). Thus, the "effective amount" of the ATP-diphosphohydrolase relates to the function of the ATP-diphosphohydrolase in a method in which the ATP-diphosphohydrolase is used (e.g., in a method of detecting non-microbial ATP.

Although the polyol, the buffer reagent, and/or the protein of the aqueous composition may also have a function in the method in which the ATP-diphosphohydrolase is used; as used herein, the "effective amounts" of the polyol, the buffer reagent, and the protein specifically relate to their roles in preserving ATP-diphosphohydrolase activity during storage (e.g., prior to using the ATP-diphosphohydrolase enzyme activity in a catalytic reaction) of the aqueous composition. The activity-preserving effects of the polyol, the buffer, and/or the protein components of the aqueous composition enable storage of the ATP-diphosphohydrolase-containing aqueous composition at ambient temperature (e.g., about 25° C.), above ambient temperature, or below ambient temperature.

The aqueous composition of the present disclosure includes an effective amount of at least one buffer reagent. In any embodiment, the buffer reagent is used to maintain the pH of the aqueous composition (at room temperature) at about 6.0 to about 7.2. In any embodiment, the buffer reagent is used to maintain the pH of the aqueous composition (at room temperature) at about 6.8 to about 7.2. In any embodiment, the buffer reagent is used to maintain the pH of the aqueous composition (at room temperature) at about 6.9 to about 7.1. The buffer reagent can be any suitable buffer compound having a pKa between about 6-8 or mixture of said compounds for buffering an aqueous solution at the aforementioned pH with the proviso that the buffer reagent does not substantially inhibit ATP-diphosphohydrolase enzyme activity when the reagent is present in the aqueous composition at an effective concentration (i.e., a concentration suitable to maintain the pH). Preferably, at operational concentrations in the aqueous composition, the buffer reagent also does not substantially inhibit luciferase enzyme activity when the aqueous composition contacts the luciferase enzyme. Examples of suitable buffer reagents include (4-(2-hydroxyethyl)-1-piperazineethanesulfonic acid) ("HEPES"), tris (hydroxymethyl) aminomethane) ("Tris"), succinic acid, phosphate, Tricine, ADA, ACES, PIPES, MOPS, BES, TES, a salt of any of the foregoing buffer reagents, and mixtures of any two or more of the foregoing buffer reagents. In any embodiment, the aqueous composition comprises HEPES, Tris, and succinate buffer reagents. In any embodiment, the at least one buffer reagent is present in the aqueous composition at a concentration of about 0.5 mM to about 200 mM.

In any embodiment, the pH of the aqueous composition at room temperature (i.e., circa 25° C.) is about 6.0 to about 7.2. In any embodiment, the pH of the aqueous composition at room temperature is between 6.0 and 7.2, inclusive. In any embodiment, the pH of the aqueous composition at room temperature is between 6.4 and 7.0, inclusive. In any embodiment, the pH of the aqueous composition at room temperature is about 7.0.

The aqueous composition of the present disclosure comprises an effective amount of a polyol. Polyols such as sucrose and sorbitol are known to be effective in preserving functional properties of myofibrillar proteins during frozen storage. Polyols suitable for use in the aqueous composition of the present disclosure include, but are not limited to, sorbitol, xylitol, glycerol, and mixtures thereof. Effective amounts of polyols for stabilizing proteins are known in the art. In any embodiment, the polyol is sorbitol. In any embodiment, the sorbitol is present in the aqueous composition at a concentration of about 1 mole/liter to about 1.6 moles/liter, inclusive.

The aqueous composition of the present disclosure includes ATP-diphosphohydrolase (ayprase) enzyme that catalyzes the hydrolysis of ATP to yield AMP and inorganic phosphate. In any embodiment, the ATP-diphosphohydrolase enzyme is derived from a potato extract. Advantageously, the other features (e.g., pH, buffer reagent, polyol, protein) of the aqueous composition act in concert to stabilize the ATP-diphosphohydrolase enzyme activity at temperatures above 0° C. for extended periods of time (e.g., greater than one week, greater than two weeks, greater than 3 weeks, greater than 4 weeks). "Stabilize the ATP-diphosphohydrolase enzyme activity", as used herein means that at least 90% of an initial ATP-diphosphohydrolase activity present in the aqueous composition before storage above 0° C. remains in the aqueous composition after the storage period when the activity is measured using a coupled enzyme assay with a fixed amount of ATP, luciferin, and luciferase.

The ATP-diphosphohydrolase enzyme activity is present in the aqueous composition at a concentration useful for catalyzing the rapid (e.g., within 15 minutes) decomposition of extracellular ATP to AMP and inorganic phosphate. However, preferably, the ATP-diphosphohydrolase enzyme activity is present in the aqueous composition at a concentration that does not substantially interfere with the measurement of extracellular ATP in a luciferase/luciferin reaction at pH 7.75. In any embodiment, the concentration of ATP-diphosphohydrolase enzyme activity in the aqueous composition of the present disclosure is about 250 Units per liter to about 2500 Units per liter. In any embodiment, the concentration of ATP-diphosphohydrolase enzyme activity in the aqueous composition of the present disclosure is about 600 Units per liter to about 1200 Units per liter.

The aqueous composition of the present disclosure includes an effective amount of a protein. The protein is distinct from the ATP-diphosphohydrolase enzyme present in the aqueous composition. The protein functions to stabilize the ATP-diphosphohydrolase enzyme activity at temperatures above 0° C. Nonlimiting examples of suitable proteins for use in the aqueous composition of the present disclosure include serum albumin and a purified collagen (e.g., the purified collagen sold by Sigma-Aldrich (St. Louis, Mo.) under the trade name PRIONEX®. In any embodiment, the aqueous composition comprises serum albumin. In any embodiment, the effective amount of protein (e.g., serum albumin) in the aqueous composition of the present disclosure is about 100 mg/L to about 1000 mg/L.

In any embodiment, a kit of the present disclosure optionally comprises a predetermined quantity of a somatic cell extractant. The somatic cell extractant can be used to cause lysis of somatic cells (i.e., non-microbial cells such as mammalian cells and plant cells, for example). In any embodiment of the kit, the somatic cell extractant may be provided in the kit isolated from (i.e., in a different primary container than) the aqueous composition or the kit may be provided with an effective amount of the somatic cell extractant in the aqueous composition. If provided separate from the aqueous composition, the somatic cell extractant may be provide in a powder or liquid form, either of which may be mixed, in part or entirely, with the aqueous composition to provide an effective amount of the somatic cell extractant in the aqueous composition.

In any embodiment, the somatic cell extractant may comprise a nonionic surfactant. Examples of suitable somatic cell extractants include, but are not limited to, polyethylene glycol p-(1,1,3,3-tetramethylbutyl)-phenyl ether, a polyethylene glycol monoalkyl ether, and mixtures thereof.

In any embodiment of the aqueous composition of the present disclosure, the composition does not comprise an effective amount of a microbicide (e.g., an azide compound). Effective amounts of microbicide compounds are commonly used in aqueous solutions to prevent the growth of microorganisms in the solutions. However, effective amounts of microbicide compounds, if present in the aqueous composition of the present disclosure could render the aqueous composition ineffective for use in certain embodiments of a method for detecting microbial ATP in a sample (e.g., in embodiments of the method wherein "free" or "somatic" ATP is treated with the ATP-diphosphohydrolase enzyme activity before treating the sample with a microbial cell extractant to cause release of ATP from the microbial cells).

In any embodiment of the aqueous composition of the present disclosure, the composition does not comprise an effective amount of a compound comprising a thiol or mercaptan capable of reducing disulfide bonds in a protein. Thiol-containing compounds (e.g., dithiothreitol, dithioerythritol) and mercaptans (e.g., 2-mercaptoethanol) are used in aqueous solutions to stabilize the activity of certain enzymes (e.g., proteases). Thus, in any embodiment, the aqueous composition of the present disclosure does not include an effective amount of dithiothreitol, dithioerythritol, or β-mercaptoethanol.

In any embodiment, a kit of the present disclosure optionally comprises a luciferase enzyme activity. In any embodiment, the luciferase enzyme activity can be isolated (i.e., in a separate primary container) from the aqueous composition. The luciferase enzyme activity may be provided in a lyophilized form, for example, which may be rehydrated prior to use.

In any embodiment, a kit of the present disclosure optionally comprises a microbial (e.g., bacterial) cell extractant. The bacterial cell extractant may be used with the aqueous composition of the present disclosure in a method for detecting microbial ATP in a sample. Examples of suitable microbial cell extractants include, without limitation, quaternary ammonium compounds (e.g., cetyltrimethylammonium bromide (CTAB), dodecyltrimethylammonium bromide (DTAB)) or cationic polybiguanide compounds (e.g., chlorhexidine or salts thereof). In any embodiment, the microbial cell extractant comprises chlorhexidine gluconate. In any embodiment, the bacterial cell extractant further comprises a nonionic detergent (e.g., TRITON N-60), which may facilitate cell extraction when combined with a cationic cell extractant.

In another aspect, the present disclosure provides a method. The method can be used to retain greater than or equal to 90% of an initial ATP-diphosphohydrolase enzyme activity in an aqueous composition stored above 0° C. for at least 7 days. The method comprises forming any embodiment of the aqueous composition of the present disclosure, the composition comprising effective amounts of a polyol, a buffer reagent, a protein, and ATP-diphosphohydrolase, each as disclosed herein; and storing the composition between 1-25° C., inclusive, for at least 7 days. The combination of the pH and the effective amounts of the polyol, the buffer reagent, the protein, and the ATP-diphosphohydrolase enable retention of greater than or equal to 90% of the initial ATP-diphosphohydrolase activity after the composition is held at about 25° C. from the first time point until a second time point that is at least 7 days after the first time point, wherein the ATP-diphosphohydrolase activity is measured in a bioluminescent coupled assay at pH 7.75 with non-rate-limiting concentrations of ATP, luciferin, and luciferase. An exemplary bioluminescent coupled assay ("ATP assay") for measuring ATP-diphosphohydrolase enzyme activity is described in Example 2 herein.

In any embodiment of the method, the combination of the effective amounts of the polyol, the buffer reagent, the protein, and the ATP-diphosphohydrolase enable retention of greater than or equal to 90% of the initial ATP-diphosphohydrolase activity after the composition is held at about 25° C. from the first time point until a second time point that is 14 days after the first time point. In any embodiment of the method, the combination of the effective amounts of the polyol, the buffer reagent, the protein, and the ATP-diphosphohydrolase enable retention of greater than or equal to 90% of the initial ATP-diphosphohydrolase activity after the composition is held at about 25° C. from the first time point until a second time point that is 21 days after the first time point. In any embodiment of the method, the combination of the effective amounts of the polyol, the buffer reagent, the protein, and the ATP-diphosphohydrolase enable retention of greater than or equal to 90% of the initial ATP-diphosphohydrolase activity after the composition is held at about 25° C. from the first time point until a second time point that is 28 days after the first time point. In any embodiment of the method, the combination of the pH and the effective amounts of the polyol, the buffer reagent, the protein, and the ATP-diphosphohydrolase enable retention of greater than or equal to 95% of the initial ATP-diphosphohydrolase activity after the composition is held at about 25° C. from the first time point until the second time point; wherein the second time point is 7 days, 14 days, 21 days, or 28 days after the first time point.

In another aspect, the present disclosure provides a method. The method can be used to quantify bacterial ATP in a sample. The method comprises combining a sample with any embodiment of the aqueous composition disclosed herein to form a first mixture, wherein the aqueous composition has a pH of about 6.9 to about 7.1; holding the first mixture at a predetermined temperature for a period of first time; combining the first mixture with a bacterial cell extractant, luciferase, luciferin, and a buffer reagent to form a second mixture with a pH of about 7.75; and measuring a luciferase-catalyzed bioluminescent reaction.

In any embodiment of the method, the sample can comprise an aqueous sample. In a preferred embodiment, the sample comprises milk (e.g., raw milk).

In any embodiment, the composition used in the method has a pH of about 6.8 to about 7.2. After combining the sample with the aqueous composition to form a first mixture, the first mixture is held for a period of time (e.g., about 1 minute, about 2 minutes, about 3 minutes, about 5 minutes, about 10 minutes, about 15 minutes, about 20 minutes, about 25 minutes, about 30 minutes) at a predetermined temperature (e.g., ambient temperature) in order to permit the ATP-diphosphohydrolase to hydrolyze any ATP present in the sample.

In any embodiment, combining the sample with the aqueous composition to form a first mixture optionally includes forming a first mixture comprising an effective amount of a somatic cell extractant. The somatic cell extractant can be added into the first mixture separately or it may be provided in the sample or provided in the aqueous composition, as described herein. The somatic cell extractant can be used to cause lysis of somatic cells (i.e., non-microbial cells such as mammalian cells and plant cells, for example) in the sample, as discussed herein, prior to contacting the sample with the bacterial cell extractant.

After holding the first mixture for a first period of time, the first mixture is combined with a bacterial cell extractant, luciferase, luciferin, and a buffer reagent to form a second mixture having a pH of about 7.75. Once the second mixture is formed; bacteria, if present in the sample, are lysed and their ATP is released. The released bacterial ATP can react with the luciferase and luciferin in a bioluminescent reaction that is well known in the art. The reaction can be monitored using a luminometer to determine the amount of bacterial ATP in the sample.

EXEMPLARY EMBODIMENTS

Embodiment A is a kit, comprising:
an aqueous composition having a pH of about 6.0 to about 7.2, the composition comprising effective amounts of a polyol, a buffer reagent, a protein, and ATP-diphosphohydrolase.

Embodiment B is the kit of Embodiment A, further comprising a somatic cell extractant.

Embodiment C is the kit of Embodiment A or Embodiment B, with the proviso that the composition does not include an effective amount of a microbicidal compound.

Embodiment D is the kit of Embodiment C, wherein the microbicidal compound comprises an azide moiety.

Embodiment E is the kit of any one of the preceding Embodiments, with the proviso that the composition does not include an effective amount of dithiothreitol, dithioerythritol, or β-mercaptoethanol.

Embodiment F is the kit of any one of the preceding Embodiments, further comprising a luciferase enzyme activity.

Embodiment G is the kit of Embodiment F, wherein the luciferase enzyme activity is isolated from the aqueous composition.

Embodiment H is the kit of any one of the preceding Embodiments, wherein the pH of the aqueous composition is about 6.4 to about 7.0.

Embodiment I is the kit of any one of any one of the preceding Embodiments, wherein the polyol is selected from the group consisting of sorbitol, xylitol, glycerol, and mixtures thereof.

Embodiment J is the kit of Embodiment I, wherein the polyol comprises sorbitol.

Embodiment K is the kit of Embodiment J, wherein the sorbitol is present in the aqueous composition at a concentration of about 1 mole/liter to about 1.6 moles/liter.

Embodiment L is the kit of any one of the preceding Embodiments, wherein aqueous composition comprises an effective amount of the somatic cell extractant.

Embodiment M is the kit of any one of the preceding Embodiments, wherein the somatic cell extractant comprises a nonionic surfactant.

Embodiment N is the kit of Embodiment M, wherein the somatic cell extractant is selected from the group consisting of polyethylene glycol p-(1,1,3,3-tetramethylbutyl)-phenyl ether and a polyethylene glycol monoalkyl ether.

Embodiment O is the kit of any one of the preceding Embodiments, wherein the buffer reagent comprises a mixture of HEPES and Tris succinate.

Embodiment P is the kit of any one of the preceding Embodiments, wherein the buffer reagent is present in the aqueous composition at a concentration of about 0.5 mM to about 200 mM.

Embodiment Q is the kit of any one of the preceding Embodiments, wherein the protein is selected from a group consisting of serum albumin and a purified collagen.

Embodiment R is the kit of any one of the preceding Embodiments, wherein the protein is present in the aqueous composition at a concentration of about 100 mg/L to about 1000 mg/L.

Embodiment S is the kit of any one of the preceding Embodiments, wherein the ATP-diphosphohydrolase is derived from an extract of potato.

Embodiment T is the kit of any one of the preceding Embodiments, wherein the ATP-diphosphohydrolase is present in the aqueous composition at a concentration of about 250 Units per liter to about 2500 Units per liter.

Embodiment U is the kit of any one of the preceding Embodiments, further comprising a bacterial cell extractant.

Embodiment V is the kit of embodiment U, wherein the bacterial cell extractant comprises a chlorhexidine gluconate.

Embodiment W is a method of retaining greater than or equal to 90% of an initial ATP-diphosphohydrolase enzyme activity in an aqueous composition stored above 0° C. for at least 7 days, the method comprising:

forming an aqueous composition having a pH of about 6.0 to 7.2, the composition comprising effective amounts of a polyol, a buffer reagent, a protein, and ATP-diphosphohydrolase; and storing the aqueous composition at a temperature between 1-25° C., inclusive, for a period of at least 7 days;

wherein the aqueous composition has an initial ATP-diphosphohydrolase activity at a first time point;

wherein the combination of the pH and the effective amounts of the polyol, the buffer reagent, the protein, and the ATP-diphosphohydrolase enable retention of greater than or equal to 90% of the initial ATP-diphosphohydrolase activity after the composition is held at about 25° C. from the first time point until a second time point that is at least 7 days after the first time point;

wherein the ATP-diphosphohydrolase activity is measured in a bioluminescent coupled assay at pH 7.75 with non-rate-limiting concentrations of ATP, luciferin, and luciferase.

Embodiment X is the method of Embodiment W, wherein the combination of the effective amounts of the polyol, the buffer reagent, the protein, and the ATP-diphosphohydrolase enable retention of greater than or equal to 90% of the initial ATP-diphosphohydrolase activity after the composition is held at about 25° C. from the first time point until a second time point that is 14 days after the first time point.

Embodiment Y is the method of Embodiment W, wherein the combination of the effective amounts of the polyol, the buffer reagent, the protein, and the ATP-diphosphohydrolase enable retention of greater than or equal to 90% of the initial ATP-diphosphohydrolase activity after the composition is held at about 25° C. from the first time point until a second time point that is 21 days after the first time point.

Embodiment Z is the method of Embodiment W, wherein the combination of the effective amounts of the polyol, the buffer reagent, the protein, and the ATP-diphosphohydrolase enable retention of greater than or equal to 90% of the initial ATP-diphosphohydrolase activity after the composition is held at about 25° C. from the first time point until a second time point that is 28 days after the first time point.

Embodiment AA is the method of any one of Embodiments W through Z, wherein the combination of the pH and the effective amounts of the polyol, the buffer reagent, the protein, and the ATP-diphosphohydrolase enable retention of greater than or equal to 95% of the initial ATP-diphosphohydrolase activity after the composition is held at about 25° C. from the first time point until the second time point.

Embodiment AB is a kit, comprising:

an aqueous composition having a pH of about 6.0-7.2, the composition comprising effective amounts of sorbitol, HEPES, Tris succinate, serum albumin, and ATP-diphosphohydrolase enzyme activity.

Embodiment AC is the kit of Embodiment AB, wherein in the aqueous composition, the effective amount of sorbitol is about 1.3 M, the effective amount of HEPES buffer is about 1 mM, the effective amount of Tris succinate is about 1 mM, the effective amount of serum albumin is about 230 mg/L, and the effective amount of ATP-diphosphohydrolase enzyme activity is about 600-1200 Units/liter.

Embodiment AD is the kit of Embodiment AB or Embodiment AC, further comprising a polyethylene glycol monoalkyl ether.

Embodiment AE is the kit of Embodiment AD, wherein the effective amount of polyethylene glycol monoalkyl ether is about 0.09 weight percent.

Embodiment AF is a method of quantifying bacterial ATP in a sample, the method comprising:

forming a first mixture comprising a sample and an aqueous composition;

wherein the aqueous composition has a pH of about 6.8 to about 7.2 and comprises effective amounts of a polyol, a buffer reagent, a protein, and ATP-diphosphohydrolase;

holding the first mixture at a predetermined temperature for a first period of time; combining the first mixture with a bacterial cell extractant, luciferase, luciferin, and a buffer reagent to form a second mixture with a pH of about 7.75; and measuring a luciferase-catalyzed bioluminescent reaction.

Embodiment AG is the method of Embodiment AF, wherein forming a first mixture further comprises forming a first mixture that includes an effective amount of somatic cell extractant.

Embodiment AH is the method of Embodiment AG, wherein the aqueous mixture comprises the effective amount of somatic cell extractant.

Examples

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Materials

TABLE 1

Materials used in the Examples.

| Chemical | Source |
| --- | --- |
| ATP | Part No. 10127531001; Roche Diagnostics GmbH; Mannheim, DE |
| Sorbitol | Part No. 39278657; Molekula Ltd.; Dorset, UK |

TABLE 1-continued

Materials used in the Examples.

| Chemical | Source |
|---|---|
| L/L1 (Luciferin/Luciferase) | A lyophilized composition of luciferin and luciferase; available separately with a reconstitution buffer (under Part No. 3003B) from 3M Company; St. Paul, MN |
| Lubrol | Part No. 195299; MP Biomedical; Solon, OH |
| Bovine Serum Albumin(BSA) | Part No. A4378; Sigma Chemical Co.; St. Louis, MO |
| Apyrase (from potato) | Sigma Chemical Co.; St. Louis, MN |

Reference Example 1. Stability of Lyophilized ATP-Diphosphohydrolase Enzyme Activity after Storage for Various Periods of Time at 25° C.

The current state of the art for long-term storage of apyrase is to lyophilize the enzyme. When possible, the lyophilized enzyme is stored at or below 4° C., but it can be stored for some time at ambient temperature (25° C.), as shown in this Reference Example. Vials of lyophilized ATP-diphosphohydrolase (apyrase; Part No. 62058354; 3M Company; St. Paul, Minn.) were stored at room temperature for the periods of time shown in Table 2. At each respective time point (Time Point "1" occurred the initial day of storage at ambient temperature, Time Point "2" occurred after 6-7 days of storage at ambient temperature, Time Point "3" occurred after 14-15 days of storage at ambient temperature, Time Point "4" occurred after 21-22 days of storage at ambient temperature, and Time Point "5" occurred after 28-29 days of storage at ambient temperature), one of the vials was reconstituted according to the manufacturer's instructions. The reconstituted enzyme was used in the ATP assay described below. The RLU/s was measured as described herein. The "% remaining" refers to the percentage of initial (Time Point "1") apyrase enzyme activity remaining after storage of the lyophilized enzyme at ambient temperature for each respective period of time.

Table 2. Stability of lyophilized apyrase during storage at ambient temperature. The RLU/s was measured as described herein. The "% remaining" refers to the percentage of initial (Time Point "1") apyrase enzyme activity remaining after storage at ambient temperature in each of the respective vials that were tested.

| Time Point | RLU/s | % remaining |
|---|---|---|
| 1 | 92 | 100 |
| 2 | 93.5 | 102 |
| 3 | 101.8 | 110 |
| 4 | 88 | 95.7 |
| 5 | 90 | 98 |

The results indicate the lyophilized apyrase enzyme is stable at ambient temperature for at least about 4 weeks.

Example 1. Aqueous Composition (pH 7.0) Comprising ATP-Diphosphohydrolase

An aqueous composition comprising apyrase (ATP-diphosphohydrolase) was made by mixing at room temperature the ingredients listed in Table 3. The pH of the resulting solution was adjusted to 7.0 using 1M NaOH. The resulting aqueous composition was placed in a sealed STERILIN container that was stored at ambient temperature (25° C.).

Comparative Example 1. Aqueous Composition (pH 7.75) Comprising ATP-Diphosphohydrolase An aqueous composition comprising apyrase (ATP-diphosphohydrolase) was made by mixing at room temperature the ingredients listed in Table 3. The pH of the resulting solution was adjusted to 7.75 using 1M NaOH. The resulting aqueous composition was placed in a sealed STERILIN container that was stored at ambient temperature (25° C.).

TABLE 3

Composition of ayprase formulations.

| Chemical | Amount |
|---|---|
| Sorbitol | 118.75 g |
| Lubrol | 5 g |
| HEPES | 0.12 g |
| Tris succinate | 0.18 g |
| Bovine Serum Albumin(BSA) | 0.115 g |
| Apyrase Sigma (from potato) | 300-600 Units |
| Deionized water | 422.65 g |

Stability of ATP-Diphosphohydrolase in an Aqueous Compositions Stored at 25° C.

After storage at ambient temperature for the periods of time shown in Table 4, aliquots were removed from each container (i.e., Example 1 and Comparative Example 1, and Reference Example 1) and were used in the ATP assay described below.

ATP Assay:

A vial of LL1 was reconstituted according to the manufacturer's instructions. Separate test samples for determining apyrase activity were prepared by mixing in a cuvette (at 25° C.) 600 microliters of reconstituted LL1 with 50 microliters of the aqueous apyrase composition (i.e., the composition of Example 1 or Comparative Example 1) and 50 microliters of $10^{-7}$M ATP. Immediately after preparing the samples, apyrase activity was measured in the cuvettes by following the rate of ATP decay for 8 minutes in a luminometer. The results were recorded in relative light units per second (RLU/s). A relatively higher number of RLU/s, compared to the starting time point ("Time point 1"), at each successive time point indicates retention of a larger fraction of the original apyrase enzyme activity during the storage. At time point "1" individual samples for testing apyrase activity were prepared and tested (as described above) on the same day that the individual aqueous compositions (Example 1 and Comparative Example 1) were made. At time point "2" individual 50 microliter samples for testing apyrase activity were removed from the STERILIN containers for testing (as described above) the apyrase activity in the aqueous compositions that had aged 6-7 days. At time point "3" individual 50 microliter samples for testing apyrase activity were removed from the STERILIN containers for testing (as described above) the apyrase activity in the aqueous compositions that had aged 14-15 days. At time point "4" individual 50 microliter samples for testing apyrase activity were removed from the STERILIN containers for testing (as described above) the apyrase activity in the aqueous compositions that had aged 21-22 days. At time point "5" individual 50 microliter samples for testing apyrase activity were removed from the STERILIN containers for testing (as described above) the apyrase activity in the aqueous compositions that had aged 28-29. The results are shown in Table 4.

Table 4. Stability of aqueous apyrase solutions during storage at ambient temperature. The RLU/s was measured as described herein. The "% remaining" refers to the percentage of initial (Time Point "1") apyrase enzyme activity remaining after storage at ambient temperature in each of the respective compositions that were tested.

| Time Point | Example 1 | | Comparative Example 1 | |
|---|---|---|---|---|
| | RLU/s | % remaining | RLU/s | % remaining |
| 1 | 107 | 100 | 108 | 100 |
| 2 | 105.35 | 98 | 100 | 93 |
| 3 | 108.4 | 101 | 95.8 | 89 |
| 4 | 102 | 95.3 | 108 | 100 |
| 5 | 107.2 | 100 | 82.6 | 76.5 |

The data indicate the aqueous composition having a pH of 7.0 retained significantly more ATP-diphosphohydrolase activity during storage at ambient temperature than a similar composition having a pH of 7.75.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A kit, comprising:
an aqueous composition having a pH of about 6.0 to about 7.2, the composition comprising effective amounts of a polyol, a buffer reagent, a protein, and ATP-diphosphohydrolase, wherein the ATP-diphosphohydrolase is present in the aqueous composition at a concentration of about 250 Units per liter to about 2500 Units per liter.

2. The kit of claim 1, further comprising a somatic cell extractant.

3. The kit of claim 1, with the proviso that the composition does not include an effective amount of a microbicidal compound.

4. The kit of claim 1, with the proviso that the composition does not include an effective amount of dithiothreitol, dithioerythritol, or □-mercaptoethanol.

5. The kit of claim 1, further comprising a luciferase enzyme activity.

6. The kit of claim 5, wherein the luciferase enzyme activity is isolated from the aqueous composition.

7. The kit of claim 1, wherein the pH of the aqueous composition is about 6.4 to about 7.0.

8. The kit of claim 1, wherein the polyol is selected from the group consisting of sorbitol, xylitol, glycerol, and mixtures thereof.

9. The kit of claim 8, wherein the polyol comprises sorbitol, wherein the sorbitol is present in the aqueous composition at a concentration of about 1 mole/liter to about 1.6 moles/liter.

10. The kit of claim 1, wherein aqueous composition comprises an effective amount of the somatic cell extractant.

11. The kit of claim 2, wherein the somatic cell extractant comprises a nonionic surfactant.

12. The kit of claim 11, wherein the somatic cell extractant is selected from the group consisting of polyethylene glycol p-(1,1,3,3-tetramethylbutyl)-phenyl ether and a polyethylene glycol monoalkyl ether.

13. The kit of claim 1, wherein the buffer reagent comprises a mixture of HEPES and Tris succinate.

14. The kit of claim 1, wherein the buffer reagent is present in the aqueous composition at a concentration of about 0.5 mM to about 200 mM.

15. The kit of claim 1, wherein the protein is selected from a group consisting of serum albumin and a purified collagen.

16. The kit of claim 1, further comprising a bacterial cell extractant.

17. A method of retaining greater than or equal to 90% of an initial ATP-diphosphohydrolase enzyme activity in an aqueous composition stored above 0° C. for at least 7 days, the method comprising:
forming an aqueous composition having a pH of about 6.0 to 7.2, the composition comprising effective amounts of a polyol, a buffer reagent, a protein, and ATP-diphosphohydrolase, wherein the ATP-diphosphohydrolase is present in the aqueous composition at a concentration of about 250 units per liter to about 2500 Units per liter; and
storing the aqueous composition at a temperature between 1-25° C., inclusive, for a period of at least 7 days;
wherein the aqueous composition has an initial ATP-diphosphohydrolase activity at a first time point;
wherein the combination of the pH and the effective amounts of the polyol, the buffer reagent, the protein, and the ATP-diphosphohydrolase enable retention of greater than or equal to 90% of the initial ATP-diphosphohydrolase activity after the composition is held at about 25° C. from the first time point until a second time point that is at least 7 days after the first time point;
wherein the ATP-diphosphohydrolase activity is measured at about 25° C. in a bioluminescent coupled assay at pH 7.75 with non-rate-limiting concentrations of ATP, luciferin, and luciferase.

18. The method of claim 17, wherein the combination of the pH and the effective amounts of the polyol, the buffer reagent, the protein, and the ATP-diphosphohydrolase enable retention of greater than or equal to 95% of the initial ATP-diphosphohydrolase activity after the composition is held at about 25° C. from the first time point until the second time point.

19. A method of quantifying bacterial ATP in a sample, the method comprising:
    forming a first mixture comprising a sample and an aqueous composition;
    wherein the aqueous composition has a pH of about 6.8 to about 7.2 and comprises effective amounts of a polyol, a buffer reagent, a protein, and ATP-diphosphohydrolase, wherein the ATP-diphosphohydrolase is present in the aqueous composition at a concentration of about 250 units per liter to about 2500 Units per liter;
    holding the first mixture at a predetermined temperature for a first period of time;
    combining the first mixture with a bacterial cell extractant, luciferase, luciferin, and a buffer reagent to form a second mixture with a pH of about 7.75; and
    measuring a luciferase-catalyzed bioluminescent reaction.

* * * * *

UNITED STATES PATENT AND TRADEMARK OFFICE
CERTIFICATE OF CORRECTION

PATENT NO. : 10,415,073 B2
APPLICATION NO. : 15/526087
DATED : September 17, 2019
INVENTOR(S) : Mark Driscoll It is certified that error appears in the above-identified patent and that said Letters Patent is hereby corrected as shown below:

In the Specification

Column 1, Line 67, delete ">1" and insert -- ≥1 --

Column 3, Lines 64-65, delete "ATP diphosphohydrolase" and insert -- ATP-diphosphohydrolase --

Column 5, Line 9, delete "(ayprase)" and insert -- (apyrase) --

Column 12, Line 13, delete "(ayprase)" and insert -- (apyrase) --

In the Claims

Column 14, Line 6, delete "□-mercaptoethanol." and insert -- β-mercaptoethanol. --

Signed and Sealed this
Sixth Day of October, 2020

Andrei Iancu
*Director of the United States Patent and Trademark Office*